United States Patent [19]

Almér

[11] Patent Number: 4,542,780

[45] Date of Patent: Sep. 24, 1985

[54] WAX PROFILES FOR DENTAL BRIDGES

[76] Inventor: Bengt Ö. Almér, Box 31025, 400 32 Göteborg, Sweden

[21] Appl. No.: 502,230

[22] Filed: Jun. 8, 1983

[51] Int. Cl.⁴ .............................................. B22C 7/00
[52] U.S. Cl. .................................. 164/235; 164/246; 164/34
[58] Field of Search ..................... 164/34, 35, 45, 235, 164/246; 433/213

[56] References Cited

U.S. PATENT DOCUMENTS 3,224,050 10/1962 Redtenbacher ..................... 164/246
3,344,842 10/1967 Cameron ................................ 164/34
3,661,198 5/1972 Evenson ................................ 164/34

Primary Examiner—Nicholas P. Godici
Assistant Examiner—Maureen Weikert
Attorney, Agent, or Firm—Silverman, Cass & Singer, Ltd.

[57] ABSTRACT

A wax profile for making a tooth for a dental bridge, the tooth having a cast gold alloy skeleton and porcelain coating, the skeleton being cast in a negative mold made from the wax profile and having the same shape as the wax profile. The wax profile having a wax, tooth-shaped body. The body having aligned upper and lower cavities connected vertically with a median channel to provide said porcelain coating filling the spaces of the cavities and channel with increased strength responsive to compressive forces applied vertically of the tooth.

9 Claims, 9 Drawing Figures

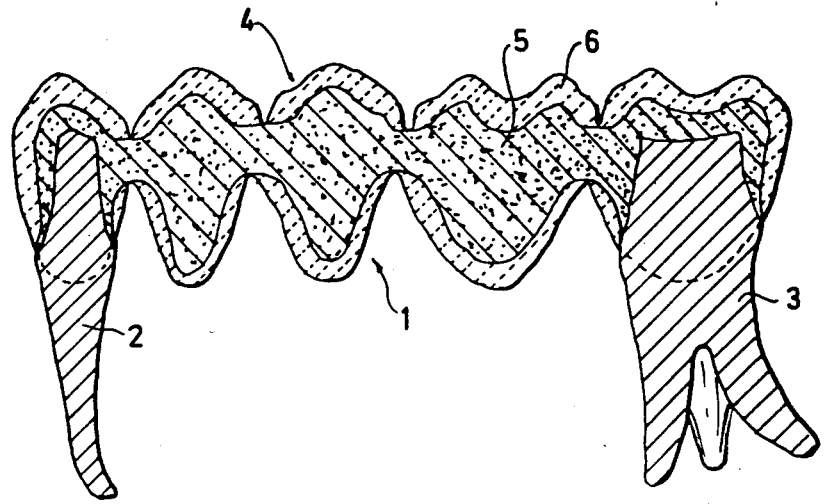
Fig_1 PRIOR ART
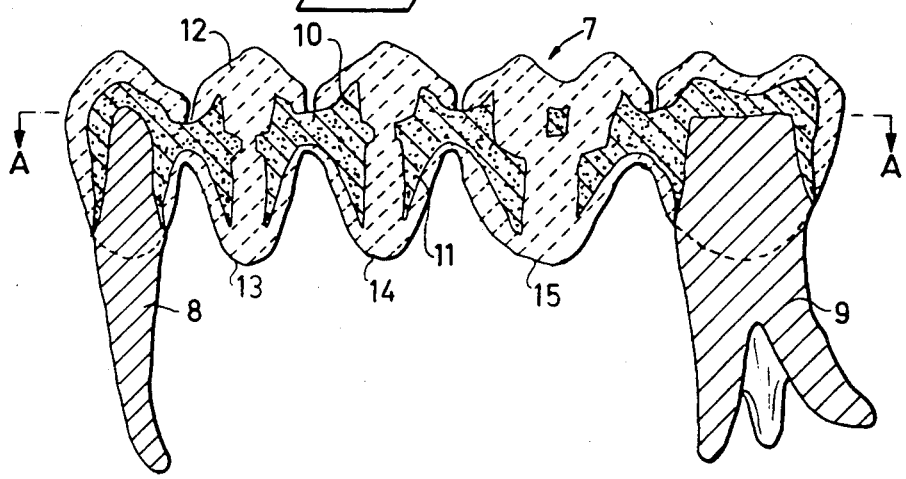
Fig_2
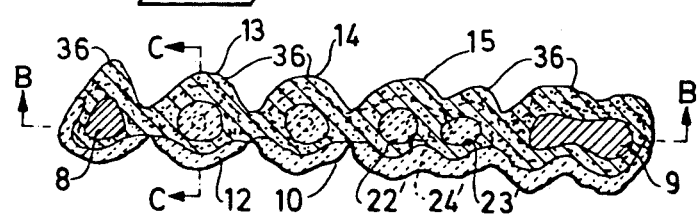
Fig_3

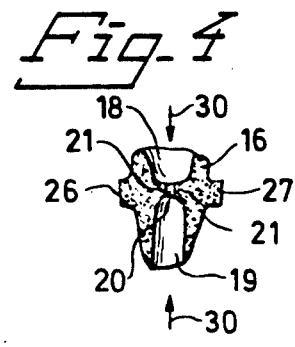
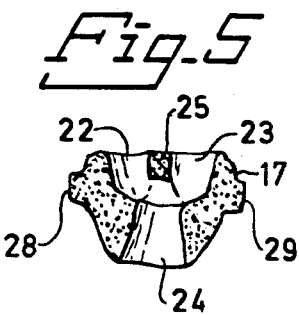
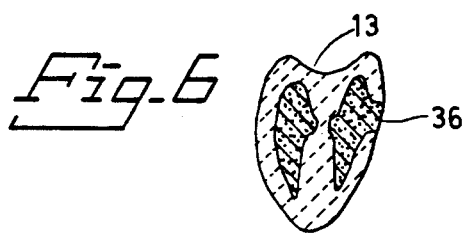
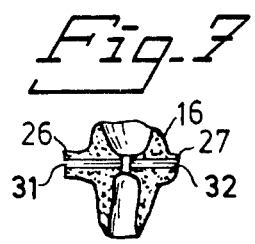
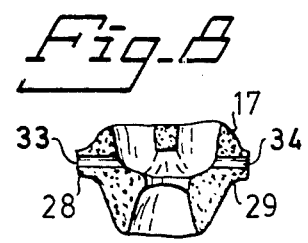
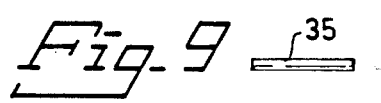

WAX PROFILES FOR DENTAL BRIDGES

The present invention is related to wax profiles for dental bridges. At present a solid skeleton of wax is constructed, which at a later stage will be moulded of a gold alloy and thus form a bridge between two teeth or parts of teeth. By replacing the wax skeleton with gold alloy, a solid gold skeleton will be produced. Such gold skeletons are relatively heavy and thus expensive.

The present invention avoids or at least limits these disadvantages considerably.

The present invention is related to wax profiles for dental bridges, these wax profiles being intended for use as models for making negatives of plaster or any other suitable material, these negatives in turn being intended for casting a gold alloy, and is characterized in that the wax profiles are tooth-shaped, in cross-section substantially round or peanut-shaped and provided with at least one inner cavity, shaped as a longitudinal tubular channel.

The invention will now be described in detail with reference to an example according to the invention shown in the attached drawing, where:

FIG. 1 is a median vertical cross-section view through a row of teeth made according to the prior art.

FIG. 2 is a median vertical cross-section view similar to that of FIG. 1, with the row of teeth made according to the present invention.

FIG. 3 is a sectional view taken along the line A—A in FIG. 2.

FIGS. 4 and 5 are two examples of wax profiles according to the invention in median vertical sections similar to the sections of FIG. 1 and FIG. 2 according to a first embodiment of the invention.

FIG. 6 is a section view taken along line C—C in FIG. 3, seen from the right in FIG. 3.

FIGS. 7 and 8 show two examples of wax profiles according to the invention in median vertical section similar to the sections of FIGS. 1 and 2 according to another embodiment of the invention.

FIG. 9 shows a rod.

FIG. 1 shows a row of teeth 1 including two tooth parts 2,3 and between these a bridge 4. In building up such a bridge a solid wax skeleton is first made and a mold of plaster is formed around the wax skeleton. A gold alloy is then cast in the negative mold of plaster. As is shown in FIG. 1. the bridge 4 is built up of a gold alloy 5, marked with dots in the FIGURES, to which a porcelain coat 6 has been applied. As mentioned previously relatively large amounts of gold are required for such a bridge.

FIG. 2 shows a section corresponding to that in FIG. 1 but according to the present invention. The row of teeth 7 in FIG. 2 includes two tooth parts 8,9 and between these parts a bridge 10. The bridge is supported by a skeleton of a gold alloy 11. In FIG. 2 as in FIG. 1 gold is marked as dotted areas. A porcelain coat 12 has been applied to the gold skeleton 11.

FIG. 3 shows a section view seen from above along line A—A in FIG. 2. FIG. 2 is a section view taken along line B—B in FIG. 3.

FIGS. 1-3 thus show built-up bridges. The present invention relates to wax profiles which are used to build up such bridges, which simplify the work considerably and which require a smaller amount of gold than a conventional bridge, as exemplified in FIG. 1.

The wax profile according to the present invention is intended to be the model around which a mold of plaster or any other suitable material is molded to form a negative mold for casting. The wax is then melted away and gold is cast in the plaster mold to a shape corresponding to the original shape of the wax profile.

According to the invention the wax profiles have bodies that are tooth-shaped and their cross-sections (See FIG. 3) are substantially round, i.e. single lobed, or peanut-shaped, i.e. double lobed, depending on the kind of tooth that is to be made. In FIGS. 2 and 3 numerals 13 and 14 represent teeth substantially round in cross-section, whilst numeral 15 represents a substantially peanut-shaped tooth, e.g. a molar.

FIG. 4 shows a section, corresponding to the section according to FIG. 2, of a wax profile body 16 for a round or single lobed tooth 13, 14. FIG. 5 shows a wax profile body 17 for a peanut-shaped or double lobed tooth 15.

According to the invention the wax profile bodies 16,17 are provided with at least one inner cavity, shaped like a tubular channel.

When the wax profile body 16 is intended for a round tooth, as for example teeth 13,14, the cavity of the wax profile comprises aligned upper and lower cavities 18,19 which are vertically connected with a median tubular channel 20 with a smaller diameter than channels 18,19. Thus a circular flange 21 is formed. Upper cavity 18 opens to the top of the body 16 and lower cavity 19 opens to the bottom of the body 16.

When the wax profile body 17 is intended for a tooth of the type numbered 15 or a similar big tooth which is substantially peanut-shaped or double lobed, the broadest part of the wax profile body 17 is provided with two parallel, first or upper cavities 22,23. The narrower part of the wax profile body 17 is provided with a second or lower cavity 24, which is parallel to and placed between the first cavities 22,23.

In FIG. 3 corresponding structure is indicated with primed numbers. The position of the second cavity 24' is indicated by a circle of dashes and the position of the first cavities 22,23 is indicated by unbroken circles. The first cavities 22,23 are connected axially to the second cavity 24. The part remaining between the first cavities 22,23 is marked with the numeral 25 in FIG. 5.

According to a preferred embodiment of the invention the wax profiles are provided with homogenous projections 26,27,28,29 for connection to an adjacent wax profile.

In a cross-section similar to those in FIG. 4 and FIG. 5 the cavities 18,19,22,23,24 take up 30% to 70% of the area, preferably about 50% of the area.

The cross-section shown in FIG. 4 is a section of a wax profile, built symmetrically along an axis. The wax profiles may, however, be designed with the oval form shown from above in FIGS. 4 and 5 or any other form instead of a round form.

Because of the cavities the wax profiles are thus tubular-shaped, with a volume which is considerably smaller than it would be for wax profiles without cavities. This smaller volume means a correspondingly smaller amount of gold. However, a gold skeleton built to the shape formed by the wax profiles is substantially as strong as a solid gold construction because the wax profiles are tubular shaped, as mentioned previously.

According to a second embodiment of the invention the projections mentioned above are provided with bore holes 31–34 (See FIGS. 7 and 8) to form a horizontal channel through the wax profiles. These bore holes 31–34 are intended to interlock with a rod 35 (See FIG. 9) which is pushed into each adjacent wax profile to hold them together. This embodiment of the invention thus further simplifies the construction of the bridge. The rod 35 is preferably made of porcelain or some other inexpensive refractory material that is inflexible. An alternative is to attach the rod into two gold skeletons, each comprising one tooth, and then solder the gold tubes which form the projections together.

According to another alternative the rod is inserted into wax profiles comprising one tooth each, and gold is then cast as described above. This alternative is specially advantageous when several teeth or a whole row of teeth are cast at the same time.

FIG. 6 shows a section along line C—C in FIG. 3, seen from the right in FIG. 3. In this section a member 36 can be seen that runs around half the circumference of the tooth on the lingual side and is connected to corresponding members on adjacent teeth. FIG. 3 shows the member 36 running along the whole row of teeth. Each one of the projections 26–29 on the wax profiles is according to yet another embodiment of the invention provided with a projection running round half of the wax profile in order to form the member mentioned.

Front teeth have not been dealt with above or in the drawings. For front teeth the same profile as for canine teeth is used, i.e. a substantially round wax profile.

When constructing a bridge according to the present invention a number of pre-fabricated wax profiles of suitable sizes and shapes are joined together and a negative mold of, for example, plaster is built up around them. The wax is then melted away and the gold is cast. When the gold has been cast, the plaster is removed. The cavities are preferably filled with porcelain or some other durable material which increases the strength of the gold skeleton to a level which corresponds to or exceeds the strength of a solid gold construction, especially in the direction of arrow 30 in FIG. 4, as porcelain has a high compressive strength.

Instead of pre-fabricating wax profiles for single teeth and joining these together in a construction, it may in certain cases be advantageous to prefabricate wax profiles comprising two or more teeth.

According to the invention, pre-fabricated wax profiles are built up whose shape fits the bridge to be constructed.

It is evident that the present invention solves the problem, presented at the beginning of this specification.

The shape of the wax profiles as well as the shape and placing of the cavities may, of course, vary. The cavities may, for example, be made tubular with a constant diameter or cone-shaped. As mentioned above the wax profiles may be made round or oval or given some other shape.

The invention should not be considered limited to the embodiments described above but may be varied within the scope of the attached patent claims.

I claim:

1. A wax profile for use in making a dental bridge, the wax profile adapted to be a model for a negative mold into which a gold alloy is cast to result in a skeleton having the same shape as the wax profile, the skeleton thereafter being coated with porcelain to form a tooth that can be joined into a dental bridge, said wax profile comprising:

a body formed of wax and having a shape in the form of a tooth that in horizontal cross-section presents at least one substantially round lobe, said body having at least one upper tubular cavity opening to the top thereof and at least one lower tubular cavity open to the bottom thereof, there being a median tubular channel vertically connecting together the upper and lower tubular cavities, so that said porcelain coating said skeleton is continuous vertically through said skeleton to provide the tooth with high strength response to compressive forces applied vertically to said tooth in said bridge.

2. The wax profile of claim 1 in which said median tubular channel has a smaller diameter than the tubular cavities to form of the skeleton a strengthening flange peripheral of the median tubular channel and between said upper and lower cavities.

3. The wax profile of claim 1 in which said body has a horizontal cross-section presenting two lobes and said body has two upper tubular cavities, one in each lobe, and said median tubular channel vertically connects said two upper tubular lobes to said one lower tubular cavity.

4. The wax profile of claim 3 in which said lower cavity is vertically aligned below and between said upper cavities.

5. The wax profile of claim 1 in which said upper and lower cavities are vertically aligned with one another.

6. The wax profile of claim 1 in which said body includes lateral projection adapted for attaching the wax profile to another wax profile.

7. The wax profile of claim 6 in which each said lateral projections includes a bore hole capable of accepting a rod by which two adjacent wax profiles can be joined together.

8. The wax profile of claim 1 in which said cavities are from 30 to 70 percent of the cross-section area of the body.

9. The wax profile of claim 8 in which said cavities are approximately 50 percent of the cross-section area of the body.

* * * * *